United States Patent
Lorant

(10) Patent No.: US 9,795,544 B2
(45) Date of Patent: *Oct. 24, 2017

(54) COSMETIC COMPOSITION COMPRISING SILICA AEROGEL PARTICLES, A GEMINI SURFACTANT AND A SOLID FATTY SUBSTANCE

(71) Applicant: L'OREAL, Paris (FR)

(72) Inventor: Raluca Lorant, Thiais (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/352,803

(22) PCT Filed: Oct. 16, 2012

(86) PCT No.: PCT/EP2012/070511
§ 371 (c)(1),
(2) Date: Apr. 18, 2014

(87) PCT Pub. No.: WO2013/057116
PCT Pub. Date: Apr. 25, 2013

(65) Prior Publication Data
US 2014/0302105 A1 Oct. 9, 2014

Related U.S. Application Data

(60) Provisional application No. 61/551,535, filed on Oct. 26, 2011.

(30) Foreign Application Priority Data

Oct. 21, 2011 (FR) ...................................... 11 59554

(51) Int. Cl.
*A61K 8/25* (2006.01)
*A61Q 19/00* (2006.01)
(Continued)

(52) U.S. Cl.
CPC .............. *A61K 8/25* (2013.01); *A61K 8/0241* (2013.01); *A61K 8/0245* (2013.01); *A61K 8/062* (2013.01); *A61K 8/31* (2013.01); *A61K 8/37* (2013.01); *A61K 8/375* (2013.01); *A61K 8/8111* (2013.01); *A61K 8/86* (2013.01); *A61K 8/922* (2013.01); *A61K 8/927* (2013.01); *A61Q 19/00* (2013.01); *A61Q 19/007* (2013.01);
(Continued)

(58) Field of Classification Search
CPC . A61K 8/25; A61K 8/927; A61K 8/86; A61K 8/062; A61K 8/8111; A61K 8/922; A61K 8/31; A61K 8/37; A61K 8/375; A61K 8/0241; A61K 8/0245; A61K 2800/412; A61K 2800/651; A61K 2800/612; A61Q 19/007; A61Q 19/00; A61Q 5/00; A61Q 19/08
See application file for complete search history.

(56) References Cited

U.S. PATENT DOCUMENTS 7,470,725 B2 12/2008 Schwertfeger et al.
2009/0105353 A1* 4/2009 Lorant ....................... 514/772.3

FOREIGN PATENT DOCUMENTS

EP 2039339 A2 3/2009
WO WO 2012/084780 A2 * 6/2012

OTHER PUBLICATIONS

"Silica Silylate Aerogel for Cosmetic Applications", ip.com Journal, ip.com Inc., West Henrietta, NY, US, Jan. 30, 2006.* Feel Enhancers & Soft Focus by the Cosmetic corporation 2012.*
International Search Report dated Aug. 22, 2013 in corresponding International Application No. PCT/EP2012/070511.

* cited by examiner

Primary Examiner — Blessing M Fubara
(74) Attorney, Agent, or Firm — Polsinelli PC

(57) ABSTRACT

The subject of the present invention is a cosmetic composition of oil-in-water type comprising: (1) hydrophobic silica aerogel particles having a specific surface area per unit of mass ($S_M$) ranging from 500 to 1500 m²/g and a size, expressed as volume-average diameter (D[0.5]), ranging from 1 to 1500 μm ; (2) at least one gemini surfactant of formula (I):

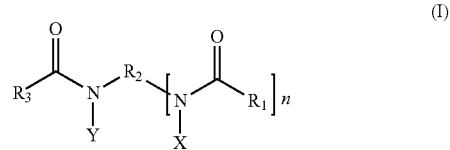

in which $R_1$ and $R_3$ denote, independently of one another, an alkyl radical containing from 1 to 25 carbon atoms; $R_2$ denotes a spacer consisting of a linear or branched alkylene chain containing from 1 to 12 carbon atoms; X and Y denote, independently of one another, a —$(C_2H_4O)_a$—$(C_3H_6O)_b$Z group; n ranges from 1 to 10 ; and (3) at least one fatty phase comprising at least one fatty substance chosen from solid fatty substances and pasty fatty substances. The composition in accordance with the invention makes it possible to make good the lack of cutaneous lipids in dehydrated skin, and to provide comfort and persistent nutrition, while at the same time having sensory properties, for example a non-greasy and non-tacky effect and a matt skin appearance, and also good skin penetration properties, even with a high level of solid fatty substance.

22 Claims, No Drawings

(51) Int. Cl.
*A61Q 19/08* (2006.01)
*A61K 8/86* (2006.01)
*A61K 8/06* (2006.01)
*A61Q 5/00* (2006.01)
*A61K 8/81* (2006.01)
*A61K 8/92* (2006.01)
*A61K 8/31* (2006.01)
*A61K 8/37* (2006.01)
*A61K 8/02* (2006.01)

(52) U.S. Cl.
CPC .. *A61K 2800/412* (2013.01); *A61K 2800/612* (2013.01); *A61K 2800/651* (2013.01); *A61Q 5/00* (2013.01); *A61Q 19/08* (2013.01)

COSMETIC COMPOSITION COMPRISING SILICA AEROGEL PARTICLES, A GEMINI SURFACTANT AND A SOLID FATTY SUBSTANCE

CROSS REFERENCE TO RELATED APPLICATIONS

This application is a National Phase filing under 35 U.S.C. §371 of PCT/EP2012/070511 filed on Oct. 16, 2012; and this application claims priority to Application No. 1159554 filed in France on Oct. 21, 2011; and this application claims the benefit of U.S. Provisional Application No. 61/551,535 filed on Oct. 26, 2011; the entire contents of all are hereby incorporated by reference.

The invention relates to a cosmetic composition of oil-in-water type intended for keratin materials, in particular the skin and the lips, the hair and the nails. The invention also relates to a cosmetic method for treating keratin materials using said composition.

Compositions rich in solid fatty substances are particularly advantageous for skin care. Indeed, they prove to be advantageous for making good the lack of cutaneous lipids in dehydrated skin, and providing comfort and persistent nutrition, but, on the other hand, can pose problems in terms of sensory properties, since they are capable of generating a greasy and tacky effect accompanied by a shiny appearance, which is not well-liked by the user.

Moreover, these products penetrate the skin with difficulty, this deficiency being all the greater, the higher the level of solid fatty substances in the composition. For example, when the level of solid fatty substances is greater than 5%, penetration is slow and is accompanied by a shiny effect of the skin which persists after the penetration of the product.

There remains the need for compositions for caring for dehydrated skin which do not have the drawbacks of the existing compositions, and in particular compositions for caring for dehydrated skin which generate a less greasy effect, penetrate rapidly and leave a matt skin appearance.

The applicant has discovered that this need can be met by combining, in a composition of emulsion type, a hydrophobic silica, a gemini surfactant and a solid fatty substance.

More specifically, a subject of the present invention is a cosmetic composition of oil-in-water type comprising:
(1) hydrophobic silica aerogel particles having a specific surface area per unit of mass ($S_M$) ranging from 500 to 1500 m²/g and a size, expressed as volume-average diameter (D[0.5]), ranging from 1 to 1500 μm ;
(2) at least one gemini surfactant of formula (I):

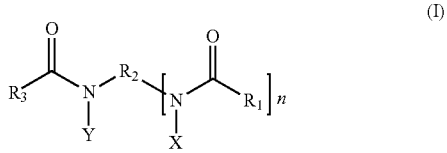

in which:
R1 and R3 denote, independently of one another, an alkyl radical containing from 1 to 25 carbon atoms;
R2 denotes a spacer consisting of a linear or branched alkylene chain containing from 1 to 12 carbon atoms;
X and Y denote, independently of one another, a —(C2H4O)a-(C3H6O)bZ group, where:

Z denotes a hydrogen atom or a —CH2—COOM, —SO3M, —P(O)(OM)2, —C2H4-SO3M, —C3H6-SO3M or —CH2(CHOH)4CH2OH radical, where M represents H or an alkali metal ion or alkaline earth metal ion or ammonium ion or alkanolammonium ion,
a ranges from 0 to 15,
b ranges from 0 to 10, and
the sum of a +b ranges from 1 to 25; and
n ranges from 1 to 10; and
(3) at least one fatty phase comprising at least one fatty substance chosen from solid fatty substances and pasty fatty substances.

As the composition of the invention is intended for topical application to the skin or superficial body growths, it comprises a physiologically acceptable medium, that is to say a medium compatible with all keratin materials, such as the skin, nails, mucous membranes and keratin fibres (such as the hair or eyelashes).

The composition in accordance with the invention makes it possible to make good the lack of cutaneous lipids in dehydrated skin, and to provide comfort and persistent nutrition, while at the same time having sensory properties, for example a non-greasy and non-tacky effect and a matt skin appearance, and also good skin penetration properties, even with a high level of solid fatty substance.

Another subject of the present invention is a cosmetic method for making up and/or caring for keratin materials comprising a step of applying a composition as defined above to said materials.

In that which follows and unless otherwise indicated, the limits of a range of values are included in this range.

Hydrophobic Silica Aerogels

Silica aerogels are porous materials obtained by replacing (by drying) the liquid component of a silica gel with air.

They are generally synthesized via a sol-gel process in liquid medium and then dried, usually by supercritical fluid extraction, the supercritical fluid most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles used in the present invention have a specific surface area per unit of mass (Sm) ranging from 500 to 1500 m2/g, preferably from 600 to 1200 m2/g and better still from 600 to 800 m2/g, and a size, expressed as volume-average diameter (D[0.5]), ranging from 1 to 1500 μm, better still from 1 to 1000 μm, preferably from 1 to 100 pm, in particular from 1 to 30 μm, more preferably from 5 to 25 μm, better still from 5 to 20 μm and even better still from 5 to 15 μm.

According to one embodiment, the hydrophobic silica aerogel particles used in the present invention have a size, expressed as volume-average diameter (D[0.5]), ranging from 1 to 30 μm, preferably from 5 to 25 μm, better still from 5 to 20 μm and even better still from 5 to 15 μm.

The specific surface area per unit of mass can be determined by the nitrogen absorption method, known as the BET (Brunauer-Emmett-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

The sizes of the silica aerogel particles may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957. According to an advantageous embodiment, the hydrophobic silica aerogel particles used in the present invention have a specific surface area per unit of mass (Sm) ranging from 600 to 800 m2/g and a size, expressed as volume-average diameter (D[0.5]), ranging from 5 to 20 pm and even better still from 5 to 15 μm.

The silica aerogel particles used in the present invention can advantageously have a packed density (p ranging from 0.04 g/cm3 to 0.10 g/cm3 and preferably from 0.05 g/cm3 to 0.08 g/cm3).

In the context of the present invention, this density, known as the packed density, may be assessed according to the following protocol:

40 g of powder are poured into a graduated measuring cylinder; the measuring cylinder is then placed on the Stay 2003 device from Stampf Volumeter; the measuring cylinder is subsequently subjected to a series of 2500 packing actions (this operation is repeated until the difference in volume between 2 consecutive tests is less than 2%); the final volume Vf of packed powder is then measured directly on the measuring cylinder. The packed density is determined by the ratio m/Vf, in this instance 40/Vf (Vf being expressed in cm3 and m in g).

According to one embodiment, the hydrophobic silica aerogel particles used in the present invention have a specific surface area per unit of volume SV ranging from 5 to 60 m2/cm3, preferably from 10 to 50 m2/cm3 and better still from 15 to 40 m2/cm3.

The specific surface area per unit of volume is given by the relationship: SV=SM×ρ where ρ is the packed density, expressed in g/cm3, and Sm is the specific surface area per unit of mass, expressed in m2/g, as defined above.

Preferably, the hydrophobic silica aerogel particles according to the invention have an oil absorption capacity, measured at the wet point, ranging from 5 to 18 ml/g, preferably from 6 to 15 ml/g and better still from 8 to 12 ml/g.

The absorption capacity measured at the wet point, noted Wp, corresponds to the amount of oil that needs to be added to 100 g of particles in order to obtain a homogeneous paste.

It is measured according to the "wet point" method or the method for determining the oil uptake of a powder described in standard NF T 30-022. It corresponds to the amount of oil adsorbed onto the available surface of the powder and/or absorbed by the powder by measurement of the wet point, described below:

An amount m=2 g of powder is placed on a glass plate, and the oil (isononyl isononanoate) is then added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The aerogels used according to the present invention are hydrophobic silica aerogels, preferably of silyl silica (INCI name: silica silylate).

The term "hydrophobic silica" is understood to mean any silica of which the surface is treated with silylating agents, for example with halogenated silanes, such as alkylchlorosilanes, siloxanes, in particular dimethylsiloxanes, such as hexamethyldisiloxane, or silazanes, so as to functionalize the OH groups with silyl Si-Rn groups, for example trimethylsilyl groups.

As regards the preparation of hydrophobic silica aerogel particles modified at the surface by silylation, reference may be made to document U.S. Pat. No. 7,470,725.

Use will in particular be made of aerogel particles of hydrophobic silica modified at the surface with trimethylsilyl groups (trimethylsiloxylated silica).

Mention may be made, as hydrophobic silica aerogels which can be used in the invention, for example, of the aerogel sold under the name VM-2260 (INCI name: Silica silylate) by the company Dow Corning, the particles of which have an average size of approximately 1000 microns and a specific surface area per unit of mass ranging from 600 to 800 m²/g.

Mention may also be made of the aerogels sold by the company Cabot under the references Aerogel TLD 201, Aerogel OGD 201 and Aerogel TLD 203.

Use will more particularly be made of the aerogel sold under the name VM-2270 (INCI name: Silica silylate) by the company Dow Corning, the particles of which have an average size ranging from 5 to 15 microns and a specific surface area per unit of mass ranging from 600 to 800 m²/g.

The hydrophobic silica aerogel particles may be present in the composition according to the invention in a content ranging from 0.05% to 15% by weight, preferably from 0.1% to 10% by weight, better still from 0.5% to 5% by weight and more preferably from 0.5% to 2% by weight relative to the total weight of the composition.

Gemini Surfactant

The gemini surfactant of formula (I) is preferably such that each of the $R_1$—CO— and $R_3$—CO— groups comprises from 8 to 20 carbon atoms and preferably denotes a coconut fatty acid residue (comprising predominantly lauric acid and myristic acid).

In addition, this surfactant is preferably such that, for each of the X and Y radicals, the sum of a and b has a mean value ranging from 10 to 20 and is preferably equal to 15. A preferred group for Z is the —$SO_3M$ group, where M is preferably an alkali metal ion, such as a sodium ion.

The spacer $R_2$ advantageously consists of a linear $C_1$-$C_3$ alkylene chain and preferably of an ethylene ($CH_2CH_2$) chain.

Finally, n is advantageously equal to 1.

A surfactant of this type is in particular that identified by the INCI name: Sodium dicocoylethylenediamine PEG-15 sulfate, having the following structure:

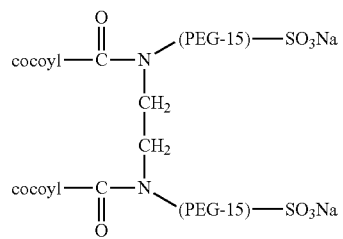

it being understood that PEG represents the $CH_2CH_2O$ group and cocoyl represents the coconut fatty acid residue.

This surfactant has a molecular structure very similar to that of ceramide-3.

Preferably, the gemini surfactant according to the invention is used as a mixture with other surfactants, and in particular as a mixture with (a) an ester of a $C_6$-$C_{22}$ fatty acid (preferably $C_{14}$-$C_{20}$ such as a stearate) and of glyceryl, (b) a diester of a $C_6$-$C_{22}$ fatty acid (preferably $C_{14}$-$C_{20}$ such as a stearate) and of citric acid and of glycerol (in particular a diester of a $C_6$-$C_{22}$ fatty acid and of glyceryl monocitrate), and (c) a $C_{10}$-$C_{30}$ fatty alcohol (preferably behenyl alcohol).

Advantageously, the composition according to the invention comprises a mixture of sodium dicocoylethylenediamine PEG-15 sulfate, of glyceryl stearate, of glyceryl stearate monocitrate and of behenyl alcohol.

More preferentially, the gemini surfactant according to the invention represents from 10 to 20% by weight and advantageously 15% by weight; the ester of a $C_6$-$C_{22}$ fatty acid and of glycerol represents from 30 to 40% by weight, advantageously 35% by weight; the diester of a $C_6$-$C_{22}$ fatty acid and of citric acid and of glycerol represents from 10 to 20% by weight, advantageously 15% by weight; and the $C_{10}$-$C_{30}$ fatty alcohol represents from 30 to 40% by weight, advantageously 35% by weight, relative to the total weight of the mixture of surfactants comprising the gemini surfactant.

Advantageously, the composition according to the invention comprises a mixture of from 10 to 20% by weight of sodium dicocoylethylenediamine PEG-15 sulfate, from 30 to 40% (in particular 35%) by weight of glyceryl stearate, from 10 to 20% (in particular 15%) by weight of glyceryl stearate monocitrate, and from 30 to 40% (in particular 35%) by weight of behenyl alcohol, relative to the total weight of the mixture of surfactants containing the gemini surfactant.

In an alternative form, the gemini surfactant according to the invention can be used as a mixture with an anionic surfactant, such as an ester of lauric acid, sodium lauroyl lactate. In this case, the gemini surfactant preferably represents from 30 to 50% by weight and the anionic surfactant represents from 50 to 70% by weight, relative to the total weight of the mixture.

The gemini surfactant may be used, for example, as a mixture with other surfactants in the form of the products sold by the company Sasol under the name Ceralution®, and in particular the following products:

Ceralution® H: Behenyl Alcohol, Glyceryl Stearate, Glyceryl Stearate Citrate and Sodium Dicocoylethylenediamine PEG-15 Sulfate, Ceralution® F: Sodium Lauroyl Lactylate and Sodium Dicocoylethylenediamine PEG-15 Sulfate, Ceralution® C: Aqua, Capric/Caprylic triglyceride, Glycerin, Ceteareth-25, Sodium Dicocoylethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben (INCI names).

This gemini surfactant represents from 3 to 50% of the weight of these mixtures.

The gemini surfactant of formula (I) may be present in a composition according to the invention in a content ranging from 0.01% to 7% by weight, preferably ranging from 0.1% to 5% by weight and better still ranging from 0.5% to 4% by weight relative to the total weight of the composition.

Fatty Phase

The proportion of the fatty phase may range, for example, from 10% to 50% by weight, preferably from 15% to 45% by weight and better still from 20% to 40% by weight relative to the total weight of the composition.

This indicated amount does not comprise the content of lipophilic surfactants.

For the purpose of the invention, the fatty phase includes any fatty substance which is liquid at ambient temperature and atmospheric pressure, generally oils, or which is solid at ambient temperature and atmospheric pressure, like waxes, or any pasty compound, which are present in said composition.

The fatty phase of the composition in accordance with the invention comprises at least one fatty substance chosen from solid fatty substances and pasty fatty substances. According to one particular embodiment of the invention, the fatty substance(s) is (are) chosen from waxes.

For the purpose of the present invention, the term "pasty fatty substance" is understood to mean a lipophilic fatty compound which undergoes a reversible solid/liquid change of state (this is not the case of all pasty compounds I believe—for example petroleum jelly is always solid, unless I am mistaken), which exhibits an anisotropic crystal organization in the solid state and which comprises, at a temperature of 23° C., a liquid fraction and a solid fraction. In other words, the starting melting point of the pasty fatty substance can be less than 23° C. The liquid fraction of the pasty fatty substance measured at 23° C. can represent from 9% to 97% by weight of the pasty fatty substance. This liquid fraction at 23° C. preferably represents between 15% and 85% and more preferably between 40% and 85% by weight.

For the purpose of the invention, the melting point corresponds to the temperature of the most endothermic peak observed on thermal analysis (DSC) as described in Standard ISO 11357-3; 1999. The melting point of a pasty fatty substance may be measured using a differential scanning calorimeter (DSC), for example the calorimeter sold under the name MDSC 2920 by the company TA Instruments.

The measuring protocol is as follows:

A sample of 5 mg of pasty fatty substance placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of pasty fatty substance is measured as a function of the temperature. The melting point of the pasty fatty substance is the value of the temperature corresponding to the tip of the peak of the curve representing the variation in the difference in power absorbed as a function of the temperature.

The liquid fraction by weight of the pasty fatty substance at 23° C. is equal to the ratio of the enthalpy of fusion consumed at 23° C. to the enthalpy of fusion of the pasty fatty substance.

The enthalpy of fusion of the pasty fatty substance is the enthalpy consumed by the latter in order to pass from the solid state to the liquid state. The pasty fatty substance is said to be in the solid state when all of its mass is in crystalline solid form. The pasty fatty substance is said to be in the liquid state when all of its mass is in liquid form.

The enthalpy of fusion of the pasty fatty substance is equal to the area under the curve of the thermogram obtained using a differential scanning calorimeter (DSC), such as the calorimeter sold under the name MDSC 2920 by the company TA Instruments, with a temperature rise of 5° C. or 10° C. per minute, according to standard ISO 11357-3:1999.

The enthalpy of fusion of the pasty fatty substance is the amount of energy required to make the pasty fatty substance change from the solid state to the liquid state. It is expressed in J/g. The enthalpy of fusion consumed at 23° C. is the amount of energy absorbed by the sample to change from the solid state to the state that it has at 23° C., composed of a liquid fraction and a solid fraction.

The liquid fraction of the pasty fatty substance measured at 32° C. preferably represents from 30% to 100% by weight of the pasty fatty substance, preferably from 50% to 100%, more preferably from 60% to 100% by weight of the pasty fatty substance. When the liquid fraction of the pasty fatty substance measured at 32° C. is equal to 100%, the temperature of the end of the melting range of the pasty fatty substance is less than or equal to 32° C.

The liquid fraction of the pasty fatty substance measured at 32° C. is equal to the ratio of the enthalpy of fusion consumed at 32° C. to the enthalpy of fusion of the pasty fatty substance. The enthalpy of fusion consumed at 32° C. is calculated in the same way as the enthalpy of fusion consumed at 23° C.

The pasty fatty substances preferably chosen from synthetic fatty substances and fatty substances of vegetable origin. A pasty fatty substance may be obtained by synthesis from starting materials of vegetable origin.

The pasty fatty substance is advantageously chosen from:
lanolin and derivatives thereof,
polyol ethers chosen from pentaerythrityl ethers of polyalkylene glycols, fatty alcohol ethers of sugars, and mixtures thereof, the pentaerythrityl ether of polyethylene glycol comprising 5 oxyethylene units (5 OE) (CTFA name: PEG-5 Pentaerythrityl Ether), the pentaerythrityl ether of polypropylene glycol comprising 5 oxypropylene units (5 OP) (CTFA name: PPG-5 Pentaerythrityl Ether), and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 Pentaerythrityl Ether, 46% PPG-5 Pentaerythrityl Ether and 8% soybean oil;
polymeric or non-polymeric silicone compounds,
polymeric or non-polymeric fluoro compounds,
vinyl polymers, in particular:
olefin homopolymers and copolymers,
hydrogenated diene homopolymers and copolymers,
liposoluble polyethers resulting from the polyetherification between one or more $C_2$-$C_{100}$ and preferably $C_2$-$C_{50}$ diols,
esters,
and/or mixtures thereof.

The pasty fatty substance is preferably a polymer, in particular a hydrocarbon-based polymer.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will in particular be made of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, isostearic acid and 12-hydroxystearic acid, especially such as the product sold under the brand name Softisan 649 by the company Sasol,
the arachidyl propionate sold under the brand name Waxenol 801 by Alzo,
phytosterol esters,
fatty acid triglycerides and derivatives thereof,
pentaerythritol esters,
esters of a diol dimer and of a diacid dimer, where appropriate esterified on their free alcohol or acid functional group(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl isostearyl dimer dilinoleate (Lusplan PI-DA, Lusplan PHY/IS-DA), phytosteryl/isostearyl/cetyl/stearyl/behenyl dimer dilinoleate (Plandool H or Plandool S), and mixtures thereof,
mango butter, such as the product sold under the reference Lipex 203 by the company AarhusKarlshamn,
hydrogenated soybean oil, hydrogenated coconut oil, hydrogenated rapeseed oil, mixtures of hydrogenated vegetable oils such as the mixture of hydrogenated soybean, coconut, palm and rapeseed vegetable oil, for example the mixture sold under the reference Akogel® by the company AarhusKarlshamn (INCI name: Hydrogenated Vegetable Oil),
shea butter, in particular the product for which the INCI name is Butyrospermum Parkii Butter, such as the product sold under the reference Sheasoft® by the company AarhusKarlshamn,
cocoa butter, in particular the product which is sold under the name CT Cocoa Butter Deodorized by the company Dutch Cocoa BV or the product which is sold under the name Beurre De Cacao NCB HD703 758 by the company Barry Callebaut,
shorea butter, in particular the product which is sold under the name Dub Shorea T by the company Stearinerie Dubois,
and mixtures thereof.

According to one preferred embodiment, the pasty fatty substance is chosen from shea butter, cocoa butter, shorea butter, a mixture of hydrogenated soybean, coconut, palm and rapeseed vegetable oils, and mixtures thereof, and more particularly those referenced above. The waxes under consideration in the context of the present invention are generally lipophilic compounds that are solid and deformable or non-deformable at ambient temperature (25° C.), with a solid/liquid reversible change of state, having a melting point of greater than or equal to 30° C., which may range up to 200° C. and in particular up to 120° C.

By bringing one or more wax(es), in accordance with the invention, to the liquid state (melting), it is possible to render it (them) miscible with one or more oils and to form a macroscopically homogeneous wax(es)+oil(s) mixture, but if the temperature of said mixture is returned to ambient temperature, recrystallization of the wax(es) in the oil(s) of the mixture is obtained.

For the purpose of the invention, the melting point corresponds to the temperature of the most endothermic peak observed on thermal analysis (DSC) as described in Standard ISO 11357-3; 1999. The melting point of the wax may be measured using a differential scanning calorimeter (DSC), for example the calorimeter sold under the name MDSC 2920 by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and it is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in a composition according to the invention are chosen from waxes, that are solid at ambient temperature, of animal, vegetable, mineral or synthetic origin, and mixtures thereof. They may be hydrocarbon-based, fluoro and/or silicone waxes.

By way of examples, mention may in particular be made of hydrocarbon-based waxes, such as natural beeswax (or bleached beeswax), synthetic beeswax, carnauba wax, rice bran wax, such as the product sold under the reference NC 1720 by the company Cera Rica Noda, candelilla wax, such as the product sold under the reference SP 75 G by the company Strahl & Pitsch, microcrystalline waxes, for instance the microcrystalline waxes of which the melting point is above 85° C., such as the products HI-MIC® 1070, 1080, 1090 et 3080 sold by the company Nippon Seiro, ceresins or ozokerites, for instance isoparaffins of which the melting point is below 40° C., such as the product EMW-0003 sold by the company Nippon Seiro, a-olefin oligomers, such as the Performa V® 825, 103 and 260 polymers sold by the company New Phase Technologies; ethylene/propylene copolymers, such as Performalene® EP 700, polyethylene waxes (preferably having a molecular weight of between 400 and 600), Fischer-Tropsch waxes, the sunflower seed wax sold by the company Koster Keunen under the reference sunflower wax.

Mention may also be made of silicone waxes, for instance alkyl or alkoxy dimethicones containing from 16 to 45 carbon atoms, and fluoro waxes.

According to one particular embodiment, the wax used in a composition in accordance with the invention has a melting point above 35° C., better still above 40° C., or even above 45° C. else above 55° C.

According to one preferred embodiment, the wax(es) is (are) chosen from polymethylene waxes; the silicone wax sold under the name Dow Corning 2501 Cosmetic Wax by the company Dow Corning (INCI name bis-peg-18 methyl ether dimethyl silane); beeswax; vegetable waxes, such as carnauba wax; the mixture of polyglycerolated (3 mol) vegetable (mimosa/jojoba/sunflower) waxes sold under the name Hydracire S by the company Gattefosse, the hydrogenated castor oil sold under the name Antisettle CVP by the company Cray Valley.

According to one particular embodiment of the invention, the fatty phase comprises at least one wax, such as carnauba wax or polymethylene wax, at least one pasty fatty substance, such as cocoa butter, and at least one oil.

The level of fatty substances chosen from solid fatty substances and pasty fatty substances in the composition can be between 2% and 20% by weight, preferably between 5% and 15% by weight relative to the total weight of the composition The fatty phase of the composition in accordance with the invention can also comprise at least one volatile or non-volatile oil.

The term "oil" is understood to mean any fatty substance that is in liquid form at ambient temperature (25° C.) and at atmospheric pressure.

The volatile or non-volatile oils may be hydrocarbon-based oils especially of animal or vegetable origin, synthetic oils, silicone oils or fluoro oils, or mixtures thereof.

For the purpose of the present invention, the term "silicone oil" is understood to mean an oil comprising at least one silicon atom, and in particular at least one Si—O group.

The term "hydrocarbon-based oil" is understood to mean an oil mainly containing hydrogen and carbon atoms, and optionally oxygen, nitrogen, sulfur and/or phosphorus atoms.

Non-Volatile Oils

For the purposes of the present invention, the term "non-volatile oil" is understood to mean an oil having a vapour pressure of less than 0.13 Pa (0.01 mmHg).

The non-volatile oils may be chosen in particular from non-volatile hydrocarbon-based oils, which may be fluorinated, and/or non-volatile silicone oils.

As non-volatile hydrocarbon-based oils that are suitable for use in the invention, mention may be made in particular of:

hydrocarbon-based oils of animal origin,
hydrocarbon-based oils of vegetable origin, such as phytostearyl esters, such as phytostearyl oleate, phytostearyl isostearate and lauroyl/octyl-dodecyl/phytostearyl glutamate, for example sold under the name Eldew PS203 by Ajinomoto, triglycerides consisting of fatty acid esters of glycerol, the fatty acids of which may have chain lengths ranging from $C_4$ to $C_{24}$, these chains possibly being linear or branched, and saturated or unsaturated; these oils are in particular heptanoic or octanoic triglycerides, wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cotton seed oil, hazelnut oil, macadamia oil, jojoba oil, alfalfa oil, poppyseed oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides, for instance those sold by the company Stearineries Dubois or those sold under the names Miglyol 810®, 812® and 818® by the company Dynamit Nobel, the refined vegetable perhydrosqualene sold under the name Fitoderm by the company Cognis;
hydrocarbon-based oils of mineral or synthetic origin, for instance:
synthetic ethers containing from 10 to 40 carbon atoms;
linear or branched hydrocarbons of mineral or synthetic origin, such as petroleum jelly, polydecenes, hydrogenated polyisobutene such as Parleam, and squalane, and mixtures thereof, and in particular hydrogenated polyisobutene;

synthetic esters, for instance oils of formula $R_1COOR_2$ in which $R_1$ represents a linear or branched fatty acid residue containing from 1 to 40 carbon atoms and $R_2$ represents a hydrocarbon-based chain that is in particular branched, containing from 1 to 40 carbon atoms provided that $R_1+R_2$ is ≥10.

The esters may in particular be chosen from esters, in particular fatty acid esters, for instance:

cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and in particular isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;

polyol esters and pentaerythritol esters, for instance dipentaerythrityl tetrahyd roxystearate/tetraisostearate;

esters of diol dimers and of diacid dimers, such as Lusplan DD-DA50 and Lusplan DD-DA7® sold by the company Nippon Fine Chemical and described in patent application FR 0302809;

fatty alcohols that are liquid at ambient temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol;

higher fatty acids such as oleic acid, linoleic acid and linolenic acid, and mixtures thereof, and dialkyl carbonates, the two alkyl chains possibly being identical or different, such as the dicaprylyl carbonate sold under the name Cetiol CC® by Cognis;

non-volatile silicone oils, for instance non-volatile polydimethylsiloxanes (PDMSs), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof;

and mixtures thereof.

Volatile Oils

For the purpose of the present invention, the term "volatile oil" is understood to mean an oil (or non-aqueous medium) that is capable of evaporating on contact with the skin in less than one hour, at ambient temperature and at atmospheric pressure. The volatile oil is a volatile cosmetic oil, which is liquid at ambient temperature, especially having a non-zero vapour pressure, at ambient temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile hydrocarbon-based oils may be chosen from hydrocarbon-based oils containing from 8 to 16 carbon atoms, and in particular branched $C_8$-$C_{16}$ alkanes (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicone oils, in particular those with a viscosity ≤8 centistokes ($8 \times 10^{-6}$ $m^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made in particular of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

It is also possible to use a mixture of the oils mentioned above.

According to one particular embodiment of the invention, the fatty phase of the composition comprises at least one fatty substance chosen from solid fatty substances and pasty fatty substances, and at least one oil.

The other fatty substances that may be present in the fatty phase are, for example, fatty acids containing from 8 to 30 carbon atoms, for instance stearic acid, lauric acid or palmitic acid; fatty alcohols containing from 8 to 30 carbon atoms, for instance stearyl alcohol or cetyl alcohol and mixtures thereof (cetearyl alcohol).

The fatty phase may also contain other compounds dissolved in the oils, such as gelling agents and/or structuring agents.

These compounds may in particular be chosen from gums, such as silicone gums (dimethiconol); silicone resins, such as trifluoromethyl($C_1$-$C_4$ alkyl) dimethicone and trifluoropropyl dimethicone, and silicone elastomers, for instance the products sold under the KSG names by the company Shin-Etsu, under the name Trefil by the company Dow Corning or under the Gransil names by the company Grant Industries; and mixtures thereof.

These fatty substances can be chosen in a varied manner by a person skilled in the art so as to prepare a composition having the desired properties, for example of consistency or texture.

Aqueous Phase

The aqueous phase of the composition according to the invention comprises at least water. According to the galenical form of the composition, the amount of aqueous phase can range from 20% to 90% by weight, preferably from 30% to 80% by weight, better still from % by weight and even better still from 40% to 70% by weight relative to the total weight of the composition. This amount depends on the galenical form of the composition desired. The amount of water can represent all or a portion of the aqueous phase and it is generally at least 30% by weight relative to the total weight of the composition.

The aqueous phase can comprise at least one hydrophilic solvent, such as, for example, substantially linear or branched lower monoalcohols having from 1 to 8 carbon atoms, such as ethanol, propanol, butanol, isopropanol or isobutanol; polyols, such as propylene glycol, isoprene glycol, butylene glycol, glycerol, sorbitol, polyethylene glycols and derivatives thereof; and mixtures thereof.

In a known way, all the compositions of the invention can comprise one or more of the adjuvants that are customary in the cosmetic and dermatological fields: hydrophilic or lipophilic gelling agents and/or thickeners; moisturisers; emollients; hydrophilic or lipophilic active agents; free radical scavengers; sequestering agents; antioxidants; preservatives; basifying or acidifying agents; fragrances; film-forming agents; and mixtures thereof.

The amounts of these various adjuvants are those conventionally used in the fields under consideration. In particular, the amounts of adjuvants vary according to the desired objective and are those conventionally used in the fields under consideration, and for example from 0.1% to 20%, and preferably from 0.5% to 10% of the total weight of the composition.

Fillers

According to one particular embodiment, the composition in accordance with the invention comprises at least one matting filler other than the hydrophobic silica aerogels.

As matting fillers that can be used in the composition of the invention, mention may be made, for example, of kaolin; and silicas, such as the polymer having the INCI name Methylsilanol/Silicate Crosspolymer, sold under the name NLK 506 by the company Takemoto Oil & Fat;

silica, such as the silica microspheres sold under the name SB 700 by the company Miyoshi Kasei; talc; boron nitride; organic spherical powders, fibres; and mixtures thereof. Examples of organic spherical powders that may be mentioned include polyamide powders and in particular Nylon® powders such as Nylon-1 or Polyamide 12, sold under the name Orgasol by the company Atochem; polyethylene powders; Teflon®; expanded powders such as hollow microspheres and especially the microspheres sold under the name Expancel by the company Kemanord Plast or under the name Micropearl F 80 ED by the company Matsumoto; silicone resin microbeads such as those sold under the name Tospearl by the company Toshiba Silicone; powders of natural organic materials such as starch powders, especially of maize starch, wheat starch or rice starch, which may or may not be crosslinked, such as the starch powders crosslinked with octenyl succinate anhydride, sold under the name Dry-Flo by the company National Starch. Examples of fibres that may be mentioned include polyamide fibres, such as in particular Nylon 6 (or Polyamide 6) (INCI name: Nylon 6) fibres, Nylon 6,6 (or Polyamide 66) (INCI name: Nylon 66) fibres, or such as poly-p-phenyleneterephthamide fibres; and mixtures thereof.

These fillers may be present in amounts ranging from 0% to 20% by weight, preferably from 0.5% to 10% by weight and even more preferentially from 0.5% to 5% by weight relative to the total weight of the composition.

Active Agents

By way of example of an active agent, mention may be made, in a nonlimiting manner, of ascorbic acid and derivatives thereof such as 5,6-di-O-diméthylsilyl ascorbate (sold by the company Exsymol under the reference PRO-AA), the potassium salt of dl-alpha-tocopheryl-2l-ascorbyl phosphate (sold by the company Senju Pharmaceutical under the reference Sepivital EPC), magnesium ascorbyl phosphate, sodium ascorbyl phosphate (sold by the company Roche under the reference Stay-C 50) ; phloroglucinol; enzymes; and mixtures thereof. According to one preferred embodiment of the invention, use is made, among oxidation-sensitive hydrophilic active agents, of ascorbic acid. The ascorbic acid can be of any nature. Thus, it can be of natural origin, in the powder form or in the form of orange juice, preferably orange juice concentrate. It can also be of synthetic origin, preferably in the powder form.

As other active agents that can be used in the composition of the invention, mention may be made, for example, of moisturising agents, such as protein hydrolysates and polyols, for instance glycerol, glycols, for instance polyethylene glycols; natural extracts; anti-inflammatories; oligomeric proanthocyanidins; vitamins such as vitamin A (retinol), vitamin E (tocopherol), vitamin B5 (panthenol), vitamin B3 (niacinamide), derivatives of these vitamins (in particular esters) and mixtures thereof; urea; caffeine; depigmenting agents such as kojic acid, hydroquinone and caffeic acid; salicylic acid and derivatives thereof; alpha-hydroxy acids, such as lactic acid and glycolic acid and derivatives thereof; retinoids, such as carotenoids and vitamin A derivatives; hydrocortisone; melatonin; extracts of algae, of fungi, of plants, of yeasts, of bacteria; steroids; antibacterial active agents, such as 2,4,4'-trichloro-2'-hydroxy diphenyl ether (or triclosan), 3,4,4'-trichlorocarbanilide (or triclocarban) and the acids indicated above, and in particular salicylic acid and derivatives thereof; matting agents, for instance fibres; tensioning agents; UV-screening agents; and mixtures thereof.

Of course, a person skilled in the art will take care to choose the optional adjuvant or adjuvants added to the composition according to the invention so that the advantageous properties intrinsically attached to the composition in accordance with the invention are not, or not substantially, detrimentally affected by the envisaged addition.

The composition according to the invention is in the form of an oil-in-water emulsion, of semi-liquid consistency of the milk type for example, obtained by dispersion of a fatty phase in an aqueous phase, or of suspensions or emulsions of soft, semi-solid or solid consistency of the cream or balm type. These compositions are prepared according to the usual methods.

In addition, the composition in accordance with the invention can be more or less thick and can have the appearance of a white or coloured cream, an ointment, a milk, a serum, a paste, a butter or a mousse.

The composition preferably exhibits a skin-friendly pH which generally ranges from 3 to 8 and preferably from 4.5 to 7.

The examples that follow will allow the invention to be understood more clearly, without, however, being limiting in nature. The raw materials are referred to by their chemical name. Unless otherwise mentioned, the amounts indicated are percentages by weight.

EXAMPLES

The gemini surfactant used in the examples hereinafter is a mixture of behenyl alcohol, glyceryl stearate, glyceryl stearate citrate and sodium dicocoylethylenediamine PEG-15 sulfate sold by the company Sasol under the name Ceralution® H.

Comparative Examples 1 and 2

Mature Skin Nutritive Butter

The following 2 compositions were prepared.

| Phase | Compositions | 1 (invention) | 2 (comparative) |
|---|---|---|---|
| A | Water | qs for 100 | qs for 100 |
|   | Preservative(s) | 0.25 | 0.25 |
|   | Glycerol | 3 | 3 |

-continued

| Phase | Compositions | 1 (invention) | 2 (comparative) |
|---|---|---|---|
| B | Gemini surfactant | 3 | 3 |
| | Isononyl isononanoate | 5 | 5 |
| | Penthaeryrtrityl tetraisostearate | 2 | 2 |
| | Hydrogenated polyisobutene | 4 | 4 |
| | cetearyl ethylhexanoate (and) isopropyl myristate | 5 | 5 |
| | Polymethylene wax sold under the name Cirebelle 303 by the company Cirebelle | 4 | 4 |
| | Carnauba wax | 2 | 2 |
| | Caprylyl methicone sold under the name Dow Corning FZ-3196 by the company Dow Corning | 1.5 | 1.5 |
| | Steareth-20 Oxyethylenated stearyl alcohol (20 EO), | 1 | 1 |
| C | Polyacrylamidomethylpropanesulfonic acid partially neutralized with aqueous ammonia and highly crosslinked, sold under the name Hostacerin AMPS by the company Clariant | 0.5 | 0.5 |
| | Xanthan gum | 0.25 | 0.25 |
| | Polydimethylsiloxane (viscosity: 5 Cst) sold under the name Xiameter PMX-200 Silicone Fluid 5CS by the company Dow Corning | 2 | 2 |
| D | Silica aerogel sold under the name VM-2270 Aerogel Fine Particles by the company Dow Corning | 1 | — |
| E | Silica microspheres sold under the name SB 700 by the company Miyoshi Kasei | 3 | 3 |

Manufacturing Process
Homogenize phase A while heating to 80° C.;
Melt phase B in a water bath and homogenize;
Form the emulsion by adding A to B at 75° C.;
Add phase C;
Cool with gentle stirring and then add the fillers D and E at 25° C.

Results of the Comparative Evaluation:

| | 1 (invention) | 2 (comparative) |
|---|---|---|
| Sensory results | Texture which melts away, spreads easily and penetrates rapidly, not very greasy, leaves the skin non-greasy and with a matt appearance | Spreading more difficult, penetrates slowly, leaves the skin tacky and shiny |

Comparative Examples 3 and 4

Anti-Aging Smoothing Care Product

The following 2 compositions were prepared.

| Phase | Compositions | 3 (invention) | 4 (comparative) |
|---|---|---|---|
| A | Water | qs for 100 | qs for 100 |
| | Preservative(s) | 0.3 | 0.3 |
| | Glycerol | 7 | 7 |
| B | Gemini surfactant | 3 | 3 |
| | Polymethylene wax sold under the name Cirebelle 303 by the company Cirebelle | 4 | 4 |
| | Carnauba wax | 0.75 | 0.75 |
| | Beeswax | 3 | 3 |
| | Pentaerythrityl tetraoctanoate | 3 | 3 |
| | Isohexadecane | 11 | 11 |
| | Hexyldecanol/hexadecyl laurate | 2 | 2 |
| | Mixture of vegetable waxes sold under the name Hydracire S by the company Gattefossé | 5 | 5 |
| | Dimethicone | 2.5 | 2.5 |
| C | Polyacrylamidomethylpropanesulfonic acid partially neutralized with aqueous ammonia and highly crosslinked, sold under the name Hostacerin AMPS by the company Clariant | 0.5 | 0.5 |
| | Xanthan gum | 0.25 | 0.25 |
| | Polydimethylsiloxane (viscosity: 5 Cst) sold under the name Xiameter PMX-200 Silicone Fluid 5CS by the company Dow Corning | 2 | 2 |
| D | Silica aerogel sold under the name VM-2270 Aerogel Fine Particles by the company Dow Corning | 0.8 | — |

-continued

| Phase | Compositions | 3 (invention) | 4 (comparative) |
|---|---|---|---|
| E | Silica microspheres sold under the name SB 700 by the company Miyoshi Kasei | 3 | 3 |

Manufacturing Process

Homogenize phase A while heating to 80° C.;
Melt phase B in a water bath and homogenize;
Form the emulsion by adding A to B at 75° C.;
Add phase C;
Cool with gentle stirring and then add the fillers D and E at 25° C.

Results of the Comparative Evaluation:

| | 3 (invention) | 4 (comparative) |
|---|---|---|
| Sensory results | Rich texture with no greasy effect, penetrates rapidly, leaves the skin non-greasy and with a matt appearance | Spreading difficult, greasy on application, penetrates slowly, leaves the skin tacky and shiny. Oily effect |

The invention claimed is:

1. Cosmetic composition of oil-in-water emulsion type comprising:
   (1) from 0.1% to 2% by weight, relative to the total weight of the composition of hydrophobic silica aerogel particles having a specific surface area per unit of mass ($S_M$) ranging from 500 to 1500 m$^2$/g and a size, expressed as volume-average diameter (D[0.5]), ranging from 1 to 1500 μm, and wherein the hydrophobic silica aerogel particles have an oil absorption capacity, measured at the wet point, ranging from 5 to 18 ml/g of particles;
   (2) from 0.01% to 7% by weight relative to the total weight of the composition of at least one gemini surfactant of formula (I):

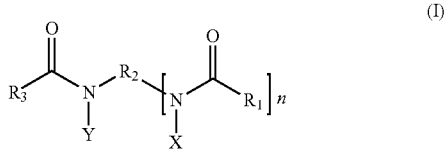

in which:
   $R_1$ and $R_3$ denote, independently of one another, an alkyl radical containing from 1 to 25 carbon atoms;
   $R_2$ denotes a spacer consisting of a linear or branched alkylene chain containing from 1 to 12 carbon atoms;
   X and Y denote, independently of one another, a $-(C_2H_4O)_a-(C_3H_6O)_b Z$ group, where:
   Z denotes a hydrogen atom or a $-CH_2-COOM$, $-SO_3M$, $-P(O)(OM)_2$, $-C_2H_4-SO_3M$, $-C_3H_6-SO_3M$ or $-CH_2(CHOH)_4CH_2OH$ radical, where M represents H or an alkali metal ion or alkaline earth metal ion or ammonium ion or alkanolammonium ion,
   a ranges from 0 to 15,
   b ranges from 0 to 10, and
   the sum of a +b ranges from 1 to 25; and
   n ranges from 1 to 10; and
   (3) at least one fatty phase comprising between 2% and 20% by weight, relative to the total weight of the composition of at least one fatty substance chosen from solid fatty substances and pasty fatty substances.

2. Composition according to claim 1, wherein each of the $R_1-CO-$ and $R_3-CO-$ groups comprises from 8 to 20 carbon atoms.

3. Composition according to claim 1, wherein, for the gemini surfactant of formula (I), for each of the X and Y radicals, the sum of a and b has a mean value ranging from 10 to 20.

4. Composition according to claim 1, wherein, for the gemini surfactant of formula (I), Z is the $-SO_3M$ group, where M is an alkali metal ion.

5. Composition according to claim 1, wherein, for the gemini surfactant of formula (I), n is equal to 1.

6. Composition according to claim 1, wherein the surfactant of formula (I) has the following structure:

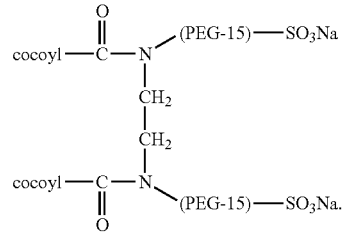

7. Composition according to claim 1, wherein the pasty fatty substance(s) is (are) chosen from a mixture of hydrogenated soybean, coconut, palm and rapeseed vegetable oils, shea butter, cocoa butter, shorea butter, and mixtures thereof.

8. Composition according to claim 1, wherein the fatty phase comprises at least one wax, at least one pasty fatty substance, and at least one oil.

9. Composition according to claim 1, wherein the level of solid fatty substances in the composition is between 2% and 20% by weight relative to the total weight of the composition.

10. Method for the cosmetic treatment of a keratin material, wherein a composition as defined in claim 1 is applied to the keratin material.

11. Composition according to claim 1, wherein the at least one matting filler other than hydrophobic silica aerogel is silica microspheres particles.

12. The composition according to claim 1, which further contains; (4) at least one matting filler other than hydrophobic silica aerogel.

13. Composition according to claim 1, wherein the hydrophobic silica aerogel particles have a specific surface area per unit of volume $S_V$ ranging from 5 to 60 m$^2$/cm$^3$.

14. Composition according to claim 13, wherein the hydrophobic silica aerogel particles are trimethylsiloxylated silica particles.

15. Composition according to claim 13, wherein each of the $R_1-CO-$ and $R_3-CO-$groups comprises from 8 to 20 carbon atoms.

16. Composition according to claim 13, wherein, for the gemini surfactant of formula (I), for each of the X and Y radicals, the sum of a and b has a mean value ranging from 10 to 20.

17. Composition according to claim 1, wherein the hydrophobic silica aerogel particles are trimethylsiloxylated silica particles.

18. Composition according to claim 17, wherein each of the $R_1$—CO— and $R_3$—CO— groups comprises from 8 to 20 carbon atoms.

19. Composition according to claim 17, wherein, for the gemini surfactant of formula (I), for each of the X and Y radicals, the sum of a and b has a mean value ranging from 10 to 20.

20. Composition according to claim 1, wherein the solid fatty substance(s) is (are) chosen from waxes.

21. Composition according to claim 20, wherein the wax(es) is (are) chosen from waxes, which are solid at ambient temperature, of animal, vegetable, mineral or synthetic origin, and mixtures thereof.

22. Composition according to claim 20, wherein the wax(es) is (are) chosen from candelilla wax, rice bran wax, sunflower seed wax and mixtures thereof.

\* \* \* \* \*